United States Patent [19]
Welsh

[11] Patent Number: 6,086,870
[45] Date of Patent: Jul. 11, 2000

[54] CO-PRECIPITATES OF ADENOVIRUS WITH METAL SALTS

[75] Inventor: Michael J. Welsh, Riverside, Iowa

[73] Assignee: The University of Iowa Research Foundation, Iowa City, Iowa

[21] Appl. No.: 09/082,510

[22] Filed: May 21, 1998

[51] Int. Cl.[7] .......................... A61K 48/00; C12N 15/12; C12N 15/861
[52] U.S. Cl. .................... 424/93.2; 435/320.1; 435/455; 435/456
[58] Field of Search ........................ 424/93.2; 435/320.1, 435/455, 456, 459

[56] References Cited

FOREIGN PATENT DOCUMENTS 9705264  2/1997  WIPO .

OTHER PUBLICATIONS

Chen et al., "High Efficiency Transformation of Mammalian Cells by Plasmid DNA," Molecular and Cellular Biology, vol. 7, No. 8, pp. 2745–2752 (1987).
Fasbender et al., "Complexes of Adenovirus with Polycationic Polymers and Cationic Lipids Increase the Efficiency of Gene Transfer in Vitro and in Vivo," Journal of Biological Chemistry, vol. 272, No. 10, pp. 6479–6489 (1997).
Graham et al., "A New Technique for the Assay of Infectivity of Human Adenovirus 5 DNA," Virology, vol. 52, pp. 456–467 (1973).
Ishiura et al., "Phage Particle–Mediated Gene Transfer to Cultured Mammalian Cells," Molecular and Cellular Biology, vol. 2, No. 6, pp. 607–616 (1982).
Jordan et al., "Transfecting Mammalian Cells: Optimization of Critical Parameters Affecting Calcium–Phosphate Precipitate Formation," Nucleic Acids Research, vol. 24, No. 4, pp. 596–601 (1996).
Loyter et al., "Mechanisms of DNA Entry into Mammalian Cells," Experimental Cell Research, vol. 139, pp. 223–234 (1982).
Morling et al., "Enhanced Transduction Efficiency of Retroviral Vectors Coprecipitated with Calcium Phosphate," Gene Therapy, vol. 2, pp. 504–508 (1995).
Pear et al., "Production of High–Titer Helper–Free Retroviruses by Transient Transfection," Proc. Natl. Acad. Sci. USA, vol. 90, pp. 8392–8396, (1993).
Wagner et al., "Delivery of Drugs, Proteins and Genes into Cells Using Transferrin as a Ligand for Receptor–Mediated Endocytosis," Advanced Drug Delivery Reviews, vol. 14, pp. 113–135 (1994).
Wilson et al., "Optimization of Calcium Phosphate Transfection for Bovine Chromaffin Cells: Relationship to Calcium Phosphate Precipitate Formation," Analytical Biochemistry, vol. 226, pp. 212–220 (1995).
Rich et al., "Development and Analysis of recombinant adenoviruses for gene therapy of cystic fibrosis", Hum. Gene Ther. 4: 461–476, Aug. 1993.

*Primary Examiner*—Scott D. Priebe
*Attorney, Agent, or Firm*—Baker Botts L.L.P.

[57] ABSTRACT

The present invention provides co-precipitates of metal salts and adenoviral vectors containing a transgene. The co-precipitates of the invention exhibit increased efficiency of gene transfer to a target cell relative to adenoviral vectors alone. Methods of making and using the co-precipitates are also provided. A method of delivering cystic fibrosis transmembrane conductance regulator to an individual with CF utilizing a co-precipitate of cationic molecules and adenoviral vectors containing a transgene encoding a CFTR protein is provided.

27 Claims, 9 Drawing Sheets

(2 of 9 Drawing Sheet(s) Filed in Color)

CO-PRECIPITATES OF ADENOVIRUS WITH METAL SALTS

FIELD OF THE INVENTION

This invention was made with government support under HL5 1670 awarded by the National Heart, Lung and Blood Institute of the National Institutes of Health. The government has certain rights in the invention.

The present invention is directed to co-precipitates of metal salts and adenoviral vectors containing transgenes. The co-precipitates of the invention exhibit increased efficiency of gene transfer relative to adenovirus alone, particularly in cells that are normally poorly infected by adenovirus.

BACKGROUND OF THE INVENTION

Effective use of transgenes for the treatment of inherited and acquired disorders requires efficient delivery of transgenes. Various vector systems have been developed that are capable of delivering a transgene to a target cell. However, there remains a need to improve efficiency of available gene transfer methods. Improved efficiency is desirable both to increase the ability of the vector to correct the cellular defect, and to decrease the required amount of the vector and thereby reduce toxicity.

Adenoviral vectors, have been designed to take advantage of the desirable features of adenovirus which render it a suitable vehicle for nucleic acid transfer. Adenovirus is a non-enveloped, nuclear DNA virus with a genome of about 36 kb, which has been well-characterized through studies in classical genetics and molecular biology (Horwitz, M. S., "Adenoviridae and Their Replication," in *Virology*, 2nd edition, Fields et al., eds., Raven Press, New York, 1990). The viral genes are classified into early (known as E1–E4) and late (known as L1–L5) transcriptional units, referring to the generation of two temporal classes of viral proteins. The demarcation between these events is viral DNA replication. The human adenoviruses are divided into numerous serotypes (approximately 47, numbered accordingly and classified into 6 subgroups: A, B, C, D, E and F), based upon properties including hemaglutination of red blood cells, oncogenicity, DNA base and protein amino acid compositions and homologies, and antigenic relationships.

Recombinant adenoviral vectors have several advantages for use as gene transfer vectors, including tropism for both dividing and non-dividing cells, minimal pathogenic potential, ability to replicate to high titer for preparation of vector stocks, and the potential to carry large inserts (Berkner, K. L., *Curr. Top. Micro. Immunol.* 158:39–66, 1992; Jolly, D., *Cancer Gene Therapv* 1:51–64, 1994).

The cloning capacity of an adenovirus vector is proportional to the size of the adenovirus genome present in the vector. For example, a cloning capacity of about 8 kb can be created from the deletion of certain regions of the virus genome dispensable for virus growth, e.g., E3, and the deletion of a genomic region such as E1 whose function may be restored in trans from 293 cells (Graham, F. L., *J. Gen. Virol.* 36:59–72, 1977) or A549 cells (Imler et al., *Gene Therapy* 3:75–84, 1996). Such E1 deleted vectors are rendered replication-defective. The upper limit of vector DNA capacity for optimal carrying capacity is about 105%–108% of the length of the wild-type genome. Further adenovirus genomic modifications are possible in vector design using cell lines which supply other viral gene products in trans, e.g., complementation of E2a (Zhou et al., *J. Virol.* 70:7030–7038, 1996), complementation of E4 (Krougliak et al., *Hum. Gene Ther.* 6:1575–1586, 1995; Wang et al., *Gene Ther.* 2:775–783, 1995), or complementation of protein IX (Caravokyri et al., *J. Virol.* 69:6627–6633, 1995; Krougliak et al., *Hum. Gene Ther.* 6:1575–1586, 1995).

Adenoviral vectors for use in gene transfer to cells and in gene therapy applications commonly are derived from adenoviruses by deletion of the early region 1 (E1) genes (Berkner, K. L., *Curr. Top. Micro. Immunol.* 158:39–66, 1992). Deletion of E1 genes renders the vector replication defective and significantly reduces expression of the remaining viral genes present within the vector. However, it is believed that the presence of the remaining viral genes in adenovirus vectors can be deleterious to the transfected cell for one or more of the following reasons: (1) stimulation of a cellular immune response directed against expressed viral proteins, (2) cytotoxicity of expressed viral proteins, and (3) replication of the vector genome leading to cell death.

Transgenes that have been expressed to date by adenoviral vectors include p53 (Wills et al., *Human Gene Therapy* 5:1079–188, 1994); dystrophin (Vincent et al., *Nature Genetics* 5:130–134, 1993; erythropoietin (Descamps et al., *Human Gene Therapy* 5:979–985, 1994; ornithine transcarbamylase (Stratford-Perricaudet et al., *Human Gene Therapy* 1:241–256, 1990; We et al., *J. Biol. Chem.* 271:3639–3646, 1996;); adenosine deaminase (Mitani et al., *Human Gene Therapy* 5:941–948, 1994); interleukin-2 (Haddada et al., *Human Gene Therapv* 4:703–711, 1993); and 60 1-antitrypsin (Jaffe et al., *Nature Genetics* 1:372–378, 1992); thrombopoietin (Ohwada et al., *Blood* 88:778–784, 1996); and cytosine deaminase (Ohwada et al., *Hum. Gene Ther.* 7:1567–1576, 1996).

The particular tropism of adenoviruses for cells of the respiratory tract has relevance to the use of adenovirus in gene transfer for cystic fibrosis (CF), which is the most common autosomal recessive disease in Caucasians. Mutations in the cystic fibrosis transmembrane conductance regulator (CFTR) gene that disturb the cAMP-regulated Cl$^-$ channel in airway epithelia result in pulmonary dysfumction (Zabner et al., *Nature Genetics* 6:75–83, 1994). Adenovirus vectors engineered to carry the CFTR gene have been developed (Rich et al., *Human Gene Therapy* 4:461–476, 1993) and studies have shown the ability of these vectors to deliver CFTR to nasal epithelia of CF patients (Zabner et al., *Cell* 75:207–216, 1993), the airway epithelia of cotton rats and primates (Zabner et al., *Nature Genetics* 6:75–83, 1994), and the respiratory epithelium of CF patients (Crystal et al., *Nature Genetics* 8:42–51, 1994). Recent studies have shown that administering an adenoviral vector containing a DNA sequence encoding CFTR to airway epithelial cells of CF patients can restore a functioning chloride ion channel in the treated epithelial cells (Zabner et al., *J. Clin. Invest.* 97:1504–1511, 1996; U.S. Pat. No. 5,670,488, issued Sep. 23, 1997).

Transfer of the cystic fibrosis transmembrane conductance regulator (CFTR) cDNA to airway epithelia of patients with cystic fibrosis (CF) thus provides an example of successful use of gene transfer to correct a cellular defect, i.e., the CF defect in electrolyte transport. Vector systems including adenoviral vectors (Zabner et al. (1993) Cell 75: 207; Knowles et al. (1995) *New Engl. J. Med.* 333: 823; Hay et al. (1995) *Hum. Gene. Ther.* 6: 1487; Zabner et al. (1996) *J. Clin. Invest.* 97: 1504 and U.S. Pat. No. 5,670,488) and cationic lipids (Caplen et al. (1995) Nat. Med. 1: 39 and U.S. Pat. No. 5,650,096) have been shown to be capable of transferring the CFTR cDNA and expressing CFTR in mature ciliated human airway epithelia. The successful delivery of CFTR in such cells is manifest in the appearance of a functional chloride ion channel in the treated cells.

While CFTR cDNA can be delivered to target cells for expression, current adenoviral vectors are less than optimal in delivering the CFTR cDNA to airway epithelia because the binding of the virus to the apical (exposed) surface of the epithelium is limited. Grubb et al. (1994) Nature 371: 802. The limited infection can be partially overcome by increasing the contact time between the virus and the apical surface. Zabner et al. (1996) J. Virol. 70: 6994.

Cationic lipid vector-mediated gene transfer to mature human airway epithelia is also suboptimal. Caplen et al. (1995) Nat. Med. 1: 39. While it appears that cationic molecules bind to the cell surface and in some cases are taken up by the cell, important barriers to transgene expression may be release of DNA from the endosome, entry into the nucleus, release of DNA from the cationic molecule, and transcription of the DNA. Zabner et al. (1995) J. Biol. Chem. 270: 18997.

Gene transfer systems that combine viral and nonviral components have been reported. Cristiano et al. (1993) Proc. Natl. Acad. Sci. USA 90: 11548; Wu et al. (1994) J. Biol. Chem. 269: 11542; Wagner et al. (1992) Proc. Natl. Acad. Sci. USA 89: 6099; Yoshimura et al. (1993) J. Biol. Chem. 268: 2300; Curiel et al. (1991) Proc. Natl. Acad. Sci USA 88: 8850; Kupfer et al. (1994) Hum. Gene Ther. 5: 1437; and Gottschalk et al. (1994) Gene Ther. 1: 185. In most cases, adenovirus has been incorporated into the gene delivery systems to take advantage of its endosomolytic properties. The reported combinations of viral and nonviral components generally involve either covalent attachment of the adenovirus to a gene delivery complex or co-internalization of unbound adenovirus with cationic lipid: DNA complexes. Further, the transferred gene is contained in plasmid DNA that is exogenous to the adenovirus. In these formulations, large amounts of adenovirus are required, and the increases in gene transfer are often modest.

Calcium phosphate is often used to facilitate entry of DNA per se into cells in transformation or transfection procedures. Transfection with calcium phosphate co-precipitates containing plasmid DNA or naked adenoviral DNA is well known for cultured cell lines (Chen et al. (1987) Mol. Cell. Biol. 7:2745–2752; Graham et al. (1973) Virol. 52: 465–477). However, such DNA calcium phosphate co-precipitates are generally ineffective in primary cell cultures and in vivo. To date, there have been no reports of calcium phosphate being used to enhance transfection with recombinant viral vectors, including adenovirus.

Accordingly, there is a need in the art for improved vector systems for the efficient delivery of transgenes to target cells. The present invention overcomes certain limitations associated with adenoviral vectors and while retaining the desirable features of the vector system.

SUMMARY OF THE INVENTION

The present invention provides co-precipitates of metal salts and adenoviral vectors in which the adenoviral vectors comprises a transgene to be delivered to a target cell or tissue. In a preferred embodiment, the cation of the metal salt is a divalent cation such as alkaline earth metals or transition-state metals, with alkaline metals being more preferred. Preferred metals include calcium, magnesium, manganese, cobalt, selenium, and zinc, with calcium being more preferred. Preferred anions of the metal salt include phosphates, carbonates and sulfides, with phosphates being more preferred. One particularly preferred metal salt precipitate to be utilized in accordance with the present invention is calcium phosphate (CaPi). Compositions comprising the co-precipitates of the invention dispersed in a carrier are also provided.

In another embodiment, the present invention is directed to a method of making a co-precipitate of the metal salt and adenoviral vectors containing a transgene by precipitating the metal salt in the presence of the adenoviral vectors to form a co-precipitate having the adenoviral vectors dispersed therein. In a preferred embodiment, the metal salt and adenoviral vectors are co-precipitated at a ratio at which gene transfer by the co-precipitate to a host cell is optimal.

In another embodiment, the present invention provides a method of delivering a transgene to a cell. The method of delivering the transgene to a cell is accomplished by precipitating metal salt in the presence of adenoviral vectors containing the transgene, and administering the co-precipitate to a cell whereby the co-precipitate facilitates cell infection and transgene expression.

The present invention also provides a method of introducing a transgene encoding a cystic fibrosis transmembrane conductance regulator (CFTR) protein into the cells of an individual with cystic fibrosis (CF). The method includes preparing a co-precipitate of metal salt and adenoviral vectors containing a transgene encoding a CFTR protein, and administering said co-precipitate to the cells of a CF patient. In a preferred embodiment the cells are airway epithelial cells.

In another embodiment, a method of providing CFTR to the airway epithelial cells of an individual with CF is provided. The method includes administering a therapeutically effective amount of a co-precipitate of the metal salt and adenoviral vectors containing a transgene encoding a CFTR protein to the airway epithelial cells of a CF patient.

DETAILED DESCRIPTION OF THE INVENTION

Figure 1A:
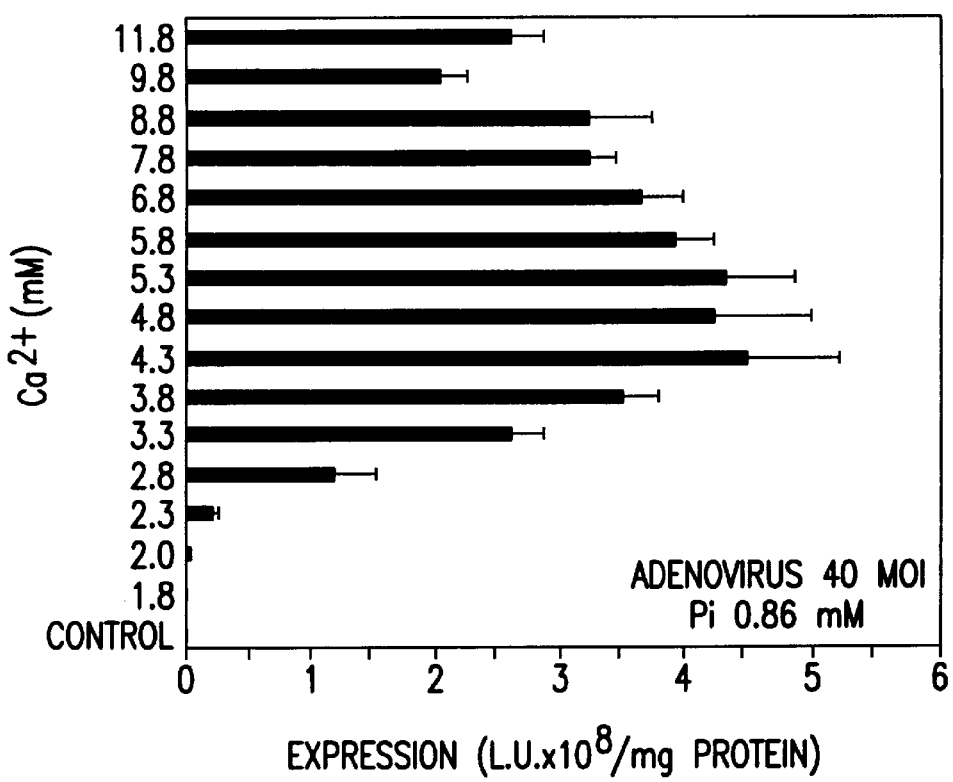
FIG. 1, Panels A–E, are bar graphs showing β-galactosidase activity of NIH 3T3 cells 24 hours after addition of adenoviral vector:calcium phosphate (Ad:CaPi) co-precipitates with one of the following variables tested over a range of values: Panel A) $Ca^{2+}$ concentration; Panel B) Pi concentration; Panel C) pH during precipitate formation; Panel D) duration of precipitate formation before addition to cells; and Panel E) MOI of adenovirus.
Figure 1B:
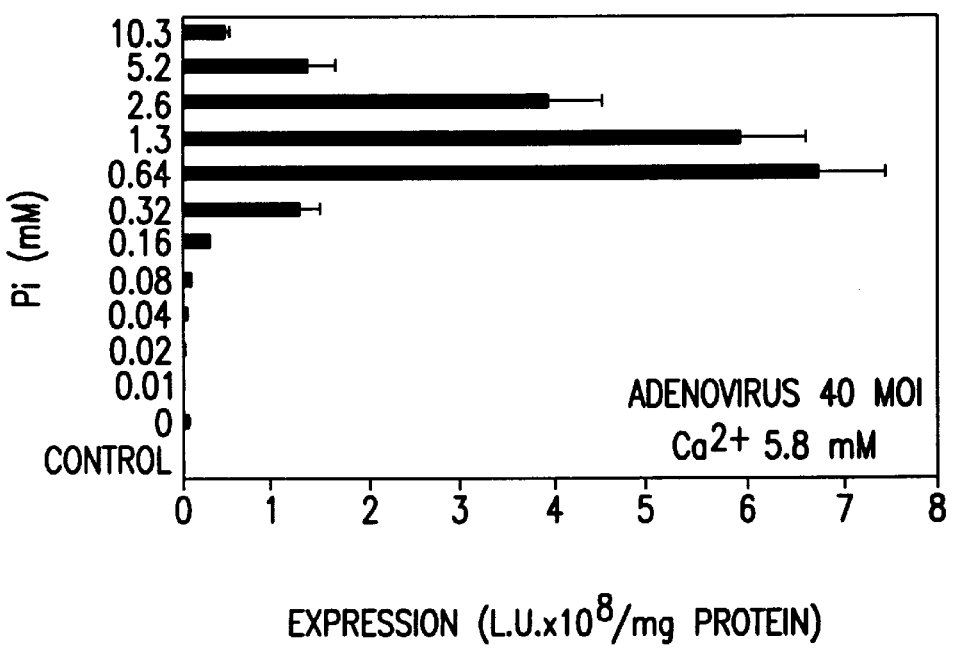
Figure 1C:
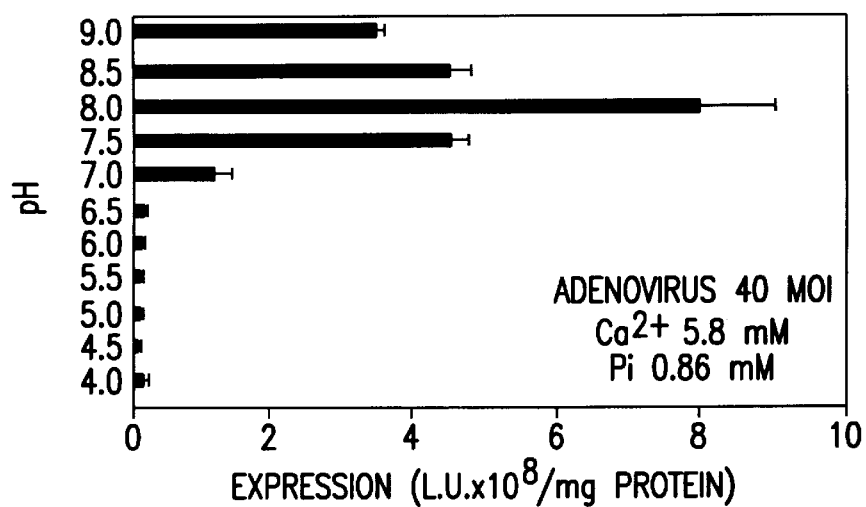
Figure 1D:
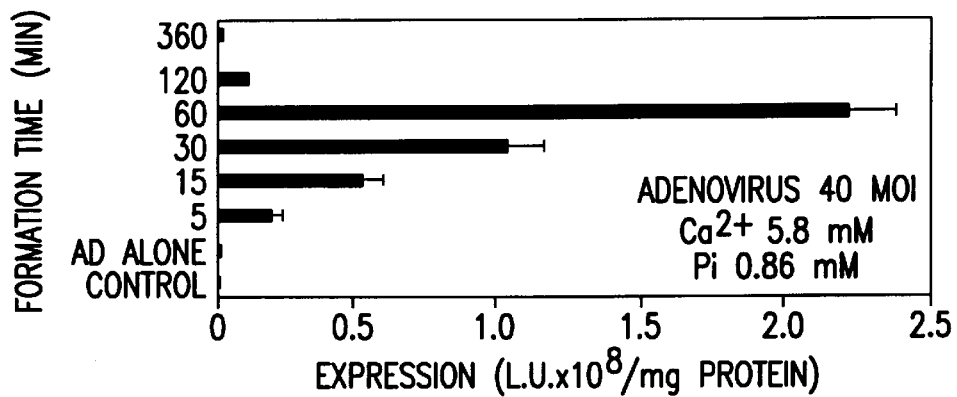
Figure 1E:
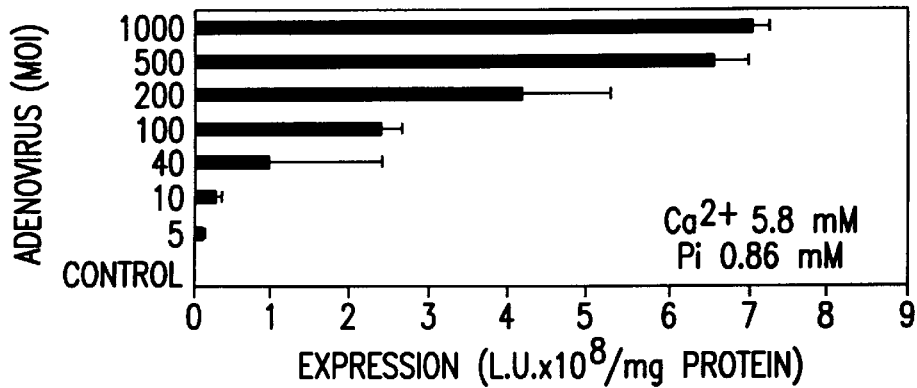

The present invention provides co-precipitates of metal salts and adenoviral vectors that are useful for the delivery of a transgene to a cell. These co-precipitates increase the binding and subsequent uptake of the adenoviral vector by a target cell or tissue. The co-precipitates are particularly useful for adenovirus-mediated gene transfer to cells that are not easily infected by adenovirus alone (i.e., adenoviral resistant cells), for example cells that do not express a cell surface receptor that binds adenovirus fiber. The adenovirus fiber molecules are found on the surface of adenovirus and are believed, inter alia, to mediate viral infectivity.

In addition, the present co-precipitates are useful for delivering an adenovirus vector to a specific cell type. In the co-precipitates of the present invention in which the metal salt masks part of the adenovirus, in particular the adenovirus fiber, the specificity of the adenovirus for its widely distributed natural targets may be reduced or eliminated. Since the adenoviral vectors within the co-precipitates retain infectivity despite masking of the fiber, the co-precipitates of the invention can be delivered to a desired target for effective transgene delivery.

In the co-precipitates of the present invention, the adenoviral vectors maintain their ability to facilitate delivery of a transgene. Transfer of a transgene to cells that are not easily infected by adenovirus alone (i.e., adenoviral resistant cells) is enhanced by the present co-precipitates.

The metal salt component of the co-precipitate of the present invention is a metal salt that forms a precipitate, in which the precipitate enhances gene transfer by an adenoviral vector to a cell type in which infection by adenovirus alone is limited. Adenoviral resistant cells include, but are not limited to, NIH-3T3 and 9L gliosarcoma cells, which are useful as in vitro model systems for assays of the co-precipitates of the invention. Other cells that are poorly infected by adenovirus, such as human endothelial cells, readily express a transgene product when treated with the co-precipitates of the present invention. A simple and convenient assay to determine the ability of a metal salt to enhance gene transfer is provided hereinbelow.

Examples of metal salt precipitates are known to those of ordinary skill in the art. In accordance with the present invention, any metal salt that forms a precipitate can be utilized as long as the precipitate is non-toxic or exhibits minimal toxicity to mammals. In a preferred embodiment, the metal is a divalent cation capable of forming a precipitate with the salt anion. Preferred divalent cations are alkaline earth metals such as calcium and magnesium, with calcium being more preferred. Other preferred divalent cations are transition-state metals such as manganese, cobalt, selenium and zinc. The anion of the metal salt is preferably phosphate, carbonate or a sulfide, with phosphate being particularly preferred. One particularly preferred metal salt precipitate that has been found to be very effective in enhancing viral infectivity and transgene expression is calcium phosphate (CaPi).

As will be apparent to one skilled in the art, the ratio of metal cations to salt anions for precipitate formation is variable and dependent on parameters such as pH of the solution, temperature and on the cations and anions selected. These parameters can easily be established from a precipitate's known solubility product ($K_{sp}$) or if unavailable by solubility curves ascertained through routine titration studies.

The co-precipitate is formed by precipitating the metal salt out of solution in the presence of the adenoviral vectors thereby forming a co-precipitate of the metal salt having the adenoviral vectors dispersed therein. For example, the adenoviral vectors can be suspended in phosphate buffered saline, at room temperature, to which a sufficient amount of a metal halide (e.g., calcium chloride) is added to precipitate the metal salt out of solution. During precipitation, the adenoviral vectors in the solution are entrapped by the forming precipitate thereby producing the co-precipitate of the invention.

Preferably, the precipitation of the metal salt is conducted using serumfree media, such as phosphate or carbonate buffered saline. The presence of serum during precipitation is disadvantageous in that it interferes with precipitate formation which significantly reduces enhanced transgene expression. While not wishing to be bound by theory, it is believed that the presence of non-adenovirus proteins and peptides in the serum interferes with precipitate formation thereby reducing the effectiveness of the co-precipitate. Thus, it is preferable to precipitate the metal salt in serum-free media to obtain a metal salt/adenoviral vector co-precipitate free of non-adenoviral proteins and peptides.

In the calcium phosphate embodiment of the present invention, precipitation is preferably conducted at a solution pH greater than 6.5, since transgene expression is generally minimalized at lower pH values as evidenced by the CaPi co-precipitates illustrated in the examples below. More preferable, the solution should be at a pH of at least 7 or greater (e.g., 8). Values of hydrogen ion concentration greater than 11, and more preferably 10, should be avoided to minimize irritation of an individual's mucosal membranes.

However, metal salt precipitates, other than calcium phosphate, that provide enhanced viral infectivity and transgene expression can be achieved at pH values of less than 6.5. Following the teachings of the present invention, metal precipitates formed at a pH less than 6.5 that provide enhanced viral infectivity and transgene expression can be easily ascertained through routine experimentation.

As will be apparent to the skilled artisan, the size of the co-precipitate is inversely proportional with reaction time. Preferably, the reaction is stopped when the precipitate has a relatively small particle size. It is believed that small partifacilitatefacilitates enhanced viral infection and transgene expression due the increased surface area provided by the particulate in comparison to the larger particulate formed if the reaction is allowed to continue where the metal salt precipitate falls to the bottom of the flask. The reaction is stopped when the solution has developed a slight haze, which indicates the formation of small particulate, by adding serum (e.g., Fetal Calf Serum) to the solution.

The adenoviral vector component of the co-precipitate of the present invention contains adenoviral DNA and a transgene of interest. The transgene is operably linked to a promoter and regulatory sequences to effect expression of the transgene in the target cell.

Adenovirus-based vectors for the delivery of transgenes are well known in the art and may be obtained commercially or constructed by standard molecular biological methods. Recombinant adenoviral vectors containing exogenous genes (transgenes) for transfer are generally derived from adenovirus type 2 (Ad2) and adenovirus type 5 (Ad5). They may also be derived from other non-oncogenic serotypes. See, e., Horowitz, *Adenoviridae and Their Replication*, in *Virology*, Second Edit., Fields, et al, Eds., Raven Press Ltd., New York, 1990, incorporated herein by reference.

The adenoviral vectors in the present invention are incapable of replicating, have minimal viral gene expression and are capable of expressing the transgene in target cells. Adenoviral vectors are generally made replication-defective by deletion of the E1 region genes. The replication-defective vectors may be produced in the 293 cell (ATCC CRL 1573), a human embryonic kidney cell line expressing E1 functions. The deleted E1 region may be replaced by the transgene of interest under the control of an adenoviral or non-adenoviral promoter. The transgene may also be placed in other regions of the adenovirus genome. Graham et al. "Adenovirus-based expression vectors and recombinant vaccines" in *Vaccines: New Approaches to Immunological Problems*, 363–390, Ellis, ed., Butteworth-Heinemann, Boston, 1992 provide a review of the production of replication-defective adenoviral vectors, and is incorporated herein by reference.

The skilled artisan is also aware that other non-essential regions of the adenovirus can be deleted or repositioned within the viral genome to provide an adenoviral vector suitable for delivery of a transgene in accordance with the present invention. For example, U.S. Pat. No. 5,670,488, the disclosure of which is incorporated herein by reference, discloses that some or all of the E1 and E3 regions may be deleted, and non-essential open reading frames of E4 can be deleted. Other representative adenoviral vectors are disclosed, for example by Rich et al. (1993) *Human Gene Therapy* 4: 461, Brody et al (1994), *Ann NY Acad Sci.* 716: 90, Wilson (1996) *New Engl. J. Med.* 334: 1185, Crystal (1995) *Science* 270: 404; O'Neal et al. (1994) *Hum. Mol. Genet.* 3: 1497; and Graham et al. (1992) in "Vaccines: New Approaches to Immunologic Problems", Butterworth-Heinemann, Boston, 363–390, the disclosures of which are incorporated herein by reference. In a preferred embodiment of the present invention, the adenoviral vector is an E1 deleted Ad2- or Ad5-based vector.

A transgene is defined herein as any nucleic acid or gene that is not native to adenovirus. Any nucleic acid that can be transcribed in the adenoviral vector is contemplated. In a preferred embodiment, the transgene encodes a biologically functional protein or peptide. A biologically functional protein or peptide is a protein or peptide that affects the cellular mechanism of a cell in which it is expressed, or the function of a tissue or an organism. For example, the biologically functional protein or peptide may be essential for normal growth or repair of a cell, for maintaining the health of an organism, or for producing a secreted protein that acts at a site distant from the cell or tissue in which it was produced. The protein or peptide may maintain or improve the health of a mammal by supplying a missing protein, by providing increased quantities of a protein that is under-produced, or by providing a protein or peptide that inhibits or counteracts an undesired molecule. Transgenes that express a biologically functional protein or peptide useful in the prevention or treatment of an inherited or acquired disorder in a mammal are particularly preferred. Examples of such biologically functional proteins include cytokines, growth factors, tumor suppressors, and clotting factors.

In one embodiment of the present invention, the transgene is DNA encoding functional cystic fibrosis transmembrane conductance regulator (CFTR) protein. CFTR is a phosphorylation and nucleoside triphosphate-regulated $Cl^-$ channel located in the apical membrane of epithelial cells in the lung, intestine, pancreas and sweat glands. For a review, see Welsh et al., (1992) *Neuron* 8: 821, incorporated herein by reference. Cystic fibrosis (CF) results from a non-functional $Cl^-$ channel in an individual's epithelial cells caused by mutations in the gene encoding CFTR. Such mutations result in loss of function of the chloride channel and thus defective electrolyte transport in affected epithelial cells. DNA encoding wild-type CFTR is known in the art; the sequence is disclosed, for example, in U.S. Pat. No. 5,670,488, incorporated herein by reference. A deletion mutant of CFTR that encodes a regulated $Cl^-$ channel is disclosed by Sheppard et al. (1994) *Cell* 76: 1091, and in, U.S. Pat. No. 5,639,661, the disclosures of which are incorporated herein by reference.

In accordance with the present invention, DNA encoding a CFTR protein includes the foregoing published sequences as well as other DNA encoding CFTR known to those of skill in the art. Further included are modifications of the known DNA molecules, for example mutations, substitutions, deletions, insertions and homologs, that encode a functional CFTR protein, i.e., a chloride channel.

DNA encoding a CFTR protein can be identified by those of ordinary skill in the art by its ability, upon expression in host cells, to correct the $Cl^-$ channel defect in cultured CF airway epithelia, for example by the methods described by Rich et al. (1990) *Nature* 347: 358, incorporated herein by reference. Briefly, cultured CF airway epithelial cells are infected with adenoviral vectors containing DNA encoding a CFTR protein. Virus-mediated expression of functional CFTR protein is assessed using an SPQ [6-methoxy-N-(3-sulfopropyl)-quinolinium, Molecular Probes, Eugene, OR] halide efflux assay. SPQ is a halide-sensitive fluorophore, the fluorescence of which is quenched by halides. In this assay, cells are loaded with SPQ, CFTR is activated by cAMP agonists, the CFTR $Cl^-$ channel opens, halides exit the cell, and SPQ fluorescence in the cell increases rapidly. Thus increases in intracellular fluorescence in response to cAMP provide a measure of a functional $Cl^-$ channel.

In another assay suitable to identify functional CFTR proteins, CF epithelial cells are infected with adenoviral vectors containing DNA encoding a CFTR protein, and secretion of $Cl^-$ from infected cells is measured in response to cAMP stimulation. The secretion of $Cl^-$ can be measured as an increase in transepithelial short-circuit current with addition of cAMP agonists, as described for example by Rich et al. (1993) *Human Gene Therapy* 4: 461, the disclosure of which is incorporated herein by reference. Expression of a functional CFTR protein can also be assessed by patch clamp techniques that detect reversibly activated whole-cell currents in response to addition of cAMP agonists, or single-channel currents in excised, cell-free patches of membrane in response to cAMP-dependent protein kinase and ATP. Patch clamp techniques are described for example by Sheppard et al. (1994) *Cell* 76: 1091, and U.S. Pat. No. 5,639,661, the disclosures of which are incorporated herein by reference.

In another embodiment, the transgene is a nucleic acid that is capable of being transcribed into an RNA molecule that is sufficiently complementary to hybridize to an mRNA or DNA of interest. Such an RNA molecule is referred to herein as an antisense molecule. Antisense molecules are useful in preventing or limiting the expression of overproduced, defective, or otherwise undesirable nucleic acid molecules.

In the adenoviral vectors of the present invention, the transgene is operably linked to expression control sequences, e.g., a promoter that directs expression of the transgene. The promoter may be an endogenous adenovirus promoter, for example the E1 a promoter or the Ad2 major late promoter (MLP) or a heterologous eucaryotic promoter, for example a phosphoglycerate kinase (PGK) promoter or a cytomegalovirus (CMV) promoter. Similarly, those of ordinary skill in the art can construct adenoviral vectors utilizing endogenous or heterologous poly A addition signals.

In accordance with the present invention, the co-precipitate is prepared by mixing the necessary components to initiate precipitation of the metal salt in the presence of the adenoviral vectors containing a transgene. The co-precipitate once formed can be dispersed with a carrier or diluent, for example, a physiological buffer, such as saline, phosphate buffered saline (PBS), water, dextrose, serum and solutions with excipients such as polyethylene glycol (PEG), propylene glycol and glycerol. Those of ordinary skill in the art appreciate that the choice of a diluent is dictated by the intended use and the route of administration for the co-precipitate. Thus, one skilled in the art can choose an appropriate diluent in accordance with known formulation principles.

The adenoviral vectors containing a transgene and the metal salt are preferably co-precipitated at a ratio that achieves optimal transfer of the transgene to a target cell or tissue. Generally, greater loading of the co-precipitate with adenoviral vectors results in greater transgene expression. The effectiveness of a specific ratio can be conveniently determined by utilizing a reporter gene (e.g., lacZ) as the transgene, preparing co-precipitates of varying ratios of adenoviral vector to metal salt, and infecting target cells with the co-precipitates. Transfer of the transgene to the target cell is evaluated by measuring the level of the transgene product in the target cell. The level of transgene product in the host cell directly correlates with the efficiency of transfer of the transgene by the co-precipitate. Expression of the transgene can be monitored by a variety of methods including, inter alia, immunological, histochemical and activity assays, depending upon the selected transgene. For example, if the transgene encodes β-galactosidase (lacZ), activity can be measured by methods well known in the art, for example by using a commercially available method such as a Galacto-Lite kit (Tropix, Inc., Bedford, Mass.) as disclosed by Zabner et al. (1996) Gene Therapy 3: 458. When the transgene is DNA encoding a CFTR protein, the presence of a functional regulated chloride channel in host cells can be determined by the methods disclosed by Sheppard et al. (1994) Cell 1: 1091 and U.S. Pat. No. 5,639,661, incorporated herein by reference. The foregoing assay for optimizing ratios is also useful for identifying cationic molecules that maximize transgene delivery.

Thus, by measuring the expression of the transgene transferred by co-precipitates of varying ratios of metal salt to adenoviral vector, a suitable ratio of a specific metal salt (e.g., CaPi) to adenoviral vectors can be determined. The ratios herein are described in terms of the total concentration of metal and salt ions per a specified number adenoviral particles. The useful ratios of metal salts per adenoviral particle vary depending upon the choice of metal salt used (e.g., $Ca_3(PO_4)_2$ versus $Mg_3(PO_4)_2$). Preferably, the metal salt precursors and adenoviral vectors are diluted and then mixed in the absence of serum at the selected ratio to form the co-precipitates of the invention. The co-precipitates are then used to transfer a transgene to a cultured cell or to a cell or tissue or organ in vivo. In a preferred embodiment, the co-precipitates are used within about five hours from the time of preparation. In a more preferred embodiment, the co-precipitates are used within from about fifteen minutes to about one hour from the time of preparation. Those skilled in the art can readily determine suitable methods for stabilizing the co-precipitates, for example using excipients such as polyethyleneglycol (PEG).

The co-precipitates of the present invention are useful for transferring a transgene to a target cell. The co-precipitates are particularly useful for the transfer of a transgene to a cell that is not easily infected by adenovirus alone (i.e., an adenoviral resistant cell). The target cell may be in vitro or in vivo. Use of the co-precipitates in vitro allows the transfer of a transgene to a cultured cell and is useful for the recombinant production of the transgene product. The co-precipitates may provide delivery of a transgene to a cell in vivo, and expression therein, for example where the transgene product is absent, insufficient, or nonfunctional. Alternately, the expression of the transgene may serve to block the expression or function of an undesired gene or gene product in the target cell.

Accordingly, the present invention provides a method of delivering a transgene to a cell. The method includes co-precipitating a metal salt with adenoviral vectors containing the transgene to form the co-precipitate, and administering the co-precipitate to a cell. In a preferred embodiment, the cell is one that is not easily infected by adenovirus alone. The co-precipitate may be administered to the cell by methods known in the art that facilitates infection of the cell. Infection of a target cell in culture is accomplished by incubating the target cell with the co-precipitate. Conditions of time, temperature, environment and culture media are standard conditions for infection of cultured cells and are within the skill of those in the art. For example, representative conditions for the infection of cultured airway epithelial cells are infection with 5,000 to 10,000 viral particles/cell, for fifteen minutes to six hours in a 5% $CO_2$ humidified environment at 37° C. Effective delivery of the transgene to the target cell can be confirmed by detecting the transgene product as described above.

Infection of a target cell in vivo is accomplished by contacting the target cell with the co-precipitate. The co-precipitate is delivered as a composition in combination with a carrier, which includes any and all solvents, diluents, isotonic agents, and the like. The use of such media and agents for preparing compositions, as provided for herein, is well known in the art. The co-precipitates of the invention may be delivered to the target cell by various delivery routes appropriate for the target cell, including for example by ingestion, injection, aerosol, inhalation, and the like. The co-precipitates may be delivered intravenously, by injection into tissue, such as brain or tumor, or by injection into a body cavity such as pleura or peritoneum. In a preferred embodiment, the transgene is a DNA molecule encoding CFTR or an analog or variant thereof (see, e.g., U.S. Pat. No. 5,639,661) which provides functional regulated chloride channel activity in target cells, and the co-precipitate is delivered to the airway epithelia by inhalation.

The present invention further provides a method of delivering a transgene encoding CFTR or variant thereof capable of forming a functional chloride channel to the cells of an individual with CF. The method includes co-precipitating the metal salt with adenoviral vectors containing the transgene encoding CFTR to form a co-precipitate, and thereafter administering said co-precipitate to the cells of an individual with CF. In a preferred embodiment the cells are airway epithelial cells. The co-precipitate may be delivered to the target cells as a composition including the co-precipitate and an acceptable carrier. The co-precipitate may be delivered to airway epithelial cells by methods known in the art, for example by inhalation or intubation and lavage. In a preferred embodiment, delivery of the co-precipitate is by inhalation.

The present invention further provides a method of providing CFTR to airway epithelial cells of individuals with CF. The method comprises combining the selected anions and cations with an adenoviral vector containing a transgene encoding CFTR to form a co-precipitate and administering the co-precipitate to epithelial cells of an individual with CF in a fashion and under conditions whereby functional $Cl^-$ channel activity is produced in the treated cells. Production of functional $Cl^-$ channels in CF patients can be evaluated by the alleviation of the symptoms associated with CF such as abnormal mucous secretion, bacterial infection, inflammation, tissue damage and fibrosis. The term "transgene encoding CFTR" includes DNA molecules that encode a $Cl^-$ channel that, when expressed in an airway epithelial cells of a CF patient, alleviate the chloride channel defect in the airway epithelial cells. In a preferred embodiment, the transgene has the sequence disclosed in U.S. Pat. No. 5,670,448 or U.S. Pat. No. 5,639,661, the disclosures of which are incorporated herein by reference.

In accordance with the present invention, co-precipitates can be formed using the adenoviral vector Ad2/CFTR-2 and administered to patients (i.e., humans) as set forth in Zabner et al. (1996) *J. Clin. Invest.* 97(6):1504–151 1, which is herein incorporated by reference. As demonstrated by Zabner et al. (1996), repeated intranasal administration of Ad2/CFTR-2 alone corrected the defect in airway epithelial $Cl^-$ transports in individuals. Ad2/CFTR-2 is an adenovirus 2-based E1 replacement vector containing the CFTR cDNA, the PGK promoter, and a synthetic bovine growth hormone poly A addition site. The vector contains the E3 region but lacks all of E4 with the exception of Open Reading Frame 6.

A metal salt co-precipitate having Ad2/CFTR-2 dispersed therein can be prepared in the following manner. Approximately $1+10^{10}$ infectious units (I.U.) is dispersed in a serum-free media such as phosphate buffered saline (PBS). While gently stirring the solution a pre-determined amount of calcium chloride ($CaCl_2$) is added to the solution. Approximately 15–30 minutes after the addition of $CaCl_2$, the solution develops a slight haze indicating that small particles of Ad2/CFTR-2:CaPi co-precipitate have formed. Serum (e.g., Fetal Calf Serum) is added to the solution to stopped further precipitation. Samples of the co-precipitate containing media can be removed and applied to the nasal epithelia of individuals suffering from CF.

The co-precipitate may be administered to the epithelial cells as a composition comprising the co-precipitate and an carrier. The co-precipitate may be administered by acceptable routes for delivery to epithelial cells. In a preferred embodiment the cells are airway epithelial cells and the co-precipitate is delivered by inhalation or intubation and lavage. For example, the composition may be administered to nasal epithelium using a modified Foley catheter, which is introduced under endoscopic guidance to the area beneath the inferior turbinate as described by Zabner et al. (1996) *J. Clin. Invest.* 97(6) 1504. Intubation and lavage is described by Welsh et al. (1995) *Human Gene Therapy* 6: 205, incorporated herein by reference. In a preferred method, the composition comprises the co-precipitate and phosphate buffered saline or other carrier and is administered by inhalation of aerosol, dry powder, or by instillation, for example by bronchoscopy.

The present invention further provides compositions comprising co-precipitates of metal salts and adenoviral vectors containing a transgene and further comprising a carrier. In a preferred embodiment the metal salt is calcium phosphate with the transgene encoding CFTR.

Where the compositions are pharmaceutical compositions, they may be prepared by techniques known in the art. The formulation of pharmaceutical compositions is generally known in the art and reference can conveniently be made to Remington's Pharmaceutical Sciences, 17th ed., Mack Publishing Co., Easton, Pa. The pharmaceutical forms of the present co-precipitates suitable for administration include sterile aqueous solutions and dispersions. The subject co-precipitates are compounded for convenient and effective administration in pharmaceutically effective amounts with a suitable pharmaceutically acceptable carrier and/or diluent in a therapeutically effective dose.

The precise effective amount of co-precipitate to be used in the methods of this invention applied to humans can be determined by the ordinary skilled artisan with consideration of individual differences in age, weight, extent of disease and condition of the individual. It can generally be stated that the preparation of the present invention should be preferably administered in an amount of at least about 1 plaque forming unit (PFU) per desired target cell.

It is especially advantageous to formulate parenteral compositions in dosage unit form for ease of administration and uniformity of dosage. Dosage unit form as used herein refers to physically discrete units suited as unitary dosages for the mammalian subjects to be treated, each unit containing a predetermined quantity of active material calculated to produce the desired phenotypic effect in association with the required carrier. The specification for the novel dosage unit forms of the invention are dictated by and directly depend on the unique characteristics of the co-precipitate and the limitations inherent in the art of compounding.

The co-precipitate is compounded for convenient and effective administration in effective amounts with a suitable carrier in dosage unit form as described above. In the case of compositions containing supplementary active ingredients, the dosages are determined by reference to the usual dose and manner of administration of the ingredients.

In the method of treatment according to the present invention, the co-precipitates may be administered in a manner compatible with the dosage formulation, in such amount as will be therapeutically effective, and in any way which is medically acceptable for the treatment of CF.

The invention is further illustrated by the following specific examples which are not intended in any way to limit the scope of the invention.

EXAMPLE 1

Materials and Methods

A. *Cell Cultures*

NIH-3T3 and COS-1 cells were cultured on 24-well plates (Corning, 25820) in Dulbecco's minimal essential media (DMEM, high glucose) supplemented with 10% fetal calf serum (FCS) (Sigma Chemical Co., St. Louis), 100 U/ml penicillin and 100 μg/ml streptomycin (P/S). HeLa cells were cultured in Eagle's minimal essential media (EMEM, Life Technologies, Inc.) supplemented with 10% FCS, 10 mM nonessential amino acids (Sigma) and P/S. Cultured cell lines were infected 18–24 hours after seeding when the cells were approximately 70% confluent. Primary cultures of normal and CF human airway epithelia were isolated and grown as described previously (Zabner et al. (1996) *J. Virol.* 70:6994–7003; Smith et al. (1996) *Cell* 85:229–236). The culture media consisted of a 1:1 mix of DMEM/Ham's F 12, 5% Ultraser G (Biosepra SA, Cedex, France), 100 U/ml penicillin and 100 μg/ml streptomycin, 1% nonessential amino acids, and 0.12 units/ml insulin. Cells were seeded on Millicell polycarbonate filters (Millipore). Twenty four hours after seeding, the cells were switched to the air-liquid interface and then grown with a dry apical surface. Epithelia were infected at least 2 weeks after seeding; transgene expression was measured 2–4 days later.

B. Vectors and Vector-Related Reagents

Recombinant adenovirus vectors (Ads) expressing μ-galactosidase, Ad2/μGal-2, and CFTR, Ad2/CFTR-16, were prepared as previously described (Zabner et al. (1996) *J. Virol.* 70:6994–7003) by the University of Iowa Gene Transfer vector Core at titers of approximately $1\times10^{10}$ I.U./ml. Ad2/CFTR-16 which is disclosed in U.S. Pat. application Ser. No. 08/839,552 filed Apr. 14, 1997, incorporated herein by reference is a recombinant Ad2 vector having an E1 and E3B deletion (but is E4+), in which the CFTR gene is under control of a CMV promoter. Other Ad vectors, e.g. Ad2/CTFR-8 (disclosed in U.S. Pat. No. 5,707,618, incorporated herein by referenced may also be used. Fiber knob protein was a gift of Dr. Paul Freimuth (Brookhaven National Laboratories, Upton, N.Y.). In some studies, adenovirus was complexed with poly-L-lysine (55 kDa, Sigma) or the cationic lipid GL-67 (a gift of Drs. Seng Cheng and David Harris, Genzyme), as described in Fasbender et al. (1997) *J. Biol. Chem.* 272:6479–6489, and U.S. patent application Ser. No. 08/755,035, filed Nov. 22, 1996. Neutralizing antibody (Virostat, 1401, Portland, Me.) or non-neutralizing antibody (MAB8052, Chemicon International Inc., Temecula, Calif.) was applied to virus in some studies. A 1:100 dilution of antibody was incubated with $2\times10^9$ particles for 30 minutes at room temperature before formation of co-precipitates.

C. Ad:CaPi Co-Precipate Formation

For the majority of the examples, CaPi co-precipitates containing adenovirus were formed by placing $8\times10^9$ particles of recombinant adenovirus in 1 ml of EMEM (M-0268, Sigma), which contains 1.8 mM $Ca^{2+}$ and 0.86 mM Pi. An aliquot of a 2 M $CaCl_2$ ($CaCl_2\times2H_2O$, E1200, Promega, Madison, Wis.) solution was added to achieve the desired $Ca^{2+}$concentration. However, a wide range of adenovirus particles and concentrations of $Ca^{2+}$ and Pi were used as described in the subsequent examples and illustrated in the Figures. The solution was mixed by vortex or gentle pipette tip aspiration. Reference to $Ca^{2+}$ and Pi concentrations refers to total ion concentration and not free ion concentration. Unless otherwise noted, the mixture was allowed to incubate for 20–30 minutes at room temperature. Then 250 μl was applied to cells for 20 minutes followed by washing the surface to remove the co-precipitate.

D. Adenovirus Tracking with Carbocvanine Dye

To evaluate virus association with cells, adenovirus was labeled with the carbocyanine dye, Cy3 (Amersham Inc., Arlington Heights, Ill.) using methods described by Drs. P. L. Leopold and R. G. Crystal (Leopold et al. (1998) *Hum. Gene Ther.* 9:367–378). Cy3 was covalently conjugated to capsid proteins of Ad2/βGal-2 by mixing 5 nmoles of Cy3 with $10^{12}$ particles of virus in 1.5 ml of $Na_2CO_3$ at pH 9.0 for 2 hours at 4° C. The solution was subsequently transferred to a dialysis chamber (Slide-A-Lyzer, 10,000 MW cutoff, Pierce Co., Rockford, Ill.) and dialyzed against two changes of phosphate-buffered saline (PBS), 3% sucrose, pH 7.4 at 4° C. for 24 hours. Expression and infection studies were performed immediately after dialysis of the conjugate. This labeling procedure decreased the I.U./particle ratio by 5–35%.

E. Evaluation of Transgene Expression and Toxicity

β-galactosidase activity was measured 24 hours after application of vector as previously described (Fasbender et al. (1997) *J. Biol. Chem.* 272:6479–6489, U.S. application Ser. No. 08/755,035) with X-gal staining of epithelia as previously described (Zabner et al. (1996) *J. Virol.* 70:6994–7003). To evaluate transepithelial electrolyte transport, epithelia were mounted in modified Ussing chambers (Zabner et al. (1996) *J. Virol.* 70:6994–7003). Short-circuit current (Isc) was measured under baseline conditions, and after addition of amiloride (10 μM), cAMP agonists (10 μM forskolin and 100 μM IBMX), and bumetanide 100 μM. Individual experiments were performed using 3 sets of cells and all experiments were repeated at least 3 times. Statistical significance was evaluated using a paired or unpaired t-test.

F. Transmission Electron Microscopy

Ad:CaPi coprecipitates were processed for transmission electron microscopy (TEM) using a negative stain technique. Fifteen-μl drops of freshly prepared samples were placed on glow-discharged collodion/carbon-coated 400-mesh copper grids for 3) minutes. The solution was wicked off with filter paper and replaced with 1% aqueous uranyl acetate for 30 s. After removal of this solution, grids were allowed to dry and imaged in a Hitachi H-7000 transmission electron microscope.

G. Murine Studies

For in vivo analysis, 6–8 week old C57BL/6 mice (Jackson Laboratories, Bar Harbor, Me.) were used. Mice were lightly anesthetized using a methoxyflurane chamber. Ad2/βGal-2 ($2\times10^8$ I.U., $5\times10^9$ particles) was administered alone or as Ad:CaPi coprecipitates intranasally in two 62.5 μl instillations delivered 5 minutes apart. The experiment was performed twice with 6 animals in each group. Three days after vector administration, animals were sacrificed. Phosphate buffered saline (PBS, 10 ml) was instilled into the right ventricle and then the lungs and heart were removed intact. The trachea was intubated and instilled at 10 cm of pressure with the following solutions in order: PBS, 4% paraformaldehyde and 0.2% gluteraldehyde, PBS, and finally X-Gal reagent for an overnight incubation at room temperature. After photography, lungs were embedded in paraffin and serially sectioned. Lung sections for each condition (n=3) were analyzed by counting all airways that were cut at a perpendicular angle. For each such airway, the airway diameter and number of blue cells (positive for B-galactoside) was determined. The percentage of blue cells was calculated as: number of blue cells÷(diameter×π÷4.9 μm). The average width of an airway cell (4.9 μm) was determined in separate experiments using hematoxylin and eosin-stained sections and is in excellent agreement with earlier studies (Mariassy, A. T. (1992) Epithelial cells of trachea and bronchi. In Comparative Biology of the Normal Lung. R. A. Parent, editor. CRC Press, Boca Raton. 63–76).

EXAMPLE 2

To ascertain whether incorporation of Ad2/μGal-2 in a precipitate would enhance adenovirus-mediated gene transfer, NIH 3T3 cells were transfected because they show little fiber receptor activity and are resistant to adenovirus infection (Seth, et al., (1994) *J. Virol.* 68:933–940). Accordingly, NIH 3T3 cells resemble the apical surface of differentiated airway epithelia and provide an in vitro model.

Standard conditions for ascertaining transgene expression of β-galactosidase were a $Ca^{2+}$ concentration of 5.8 mM, Pi concentration of 0.86 mM, pH 7.4, duration of complex formation before addition to cells of 15–30 minutes, and 40 MOI Ad2/βGal-2. The co-precipitate was applied to cells for approximately 20 minutes in each case. One of the following conditions was varied to ascertain its effect on transgene expression: A) $Ca^{2+}$ concentration; B) Pi concentration; C) pH during complex formation; D) duration of complex formation before addition to cells; and E) MOI of adenovirus. β-galactosidase activity (i.e., blue staining) was measured 24 hours after vector addition. The results of these studies are shown in FIG. 1, Panels A–E, in which each panel represents results from an experiment with n=3 and each experiment was repeated at least twice.

FIGS. 1, Panel A and Panel B show that when $Ca^{2+}$ and Pi concentrations were increased during complex formation, β-galactosidase expression increased, reached a maximum, and then decreased. These data illustrate that formation of an effective co-precipitate requires optimal stoichiometry of $Ca^{2+}$ to Pi, which can easily be ascertained by one skilled in the art. FIG. 1, Panel C shows that Ad:CaPi coprecipitates formed at acidic pH (below pH 7) provided little enhancement of gene transfer As a control for the effect of pH on the virus, HeLa cells were infected with adenovirus alone that had been exposed to the same pH as the Ad:CaPi coprecipitates; there was no effect of pH on gene transfer (not shown).

FIG. 1, Panel D shows that formation time during which $Ca^{2+}$, Pi, and adenoviral vectors were incubated before they were applied to cells influences gene transfer and transgene expression. As shown in Panel D, with increasing durations of the pre-incubation, transfection efficiency increased reaching a maximum level of efficiency at about 60 minutes. After 60 minutes, expression decreased with significantly reduced levels after 120 minutes. A time-dependent effect on precipitate formation was observed with light microscopy and visual inspection. The formation of fine precipitates was observed when infection was maximal (i.e., between 30 to 60 minutes). The development of fine precipitates provided the solution with a slight haze due to the suspended fine particles. However, with longer formation periods, macroprecipitates formed as evidenced by relatively larger particles that fell to the bottom of the vessel and gene expression decreased.

FIG. 1, Panel E shows that when the amount of virus added during precipitate formation increased (without a change in volume, $Ca^{2+}$, or Pi), gene expression increased. Thus, greater loading of the co-precipitates with adenoviral vectors resulted in greater transgene expression.

In summary, the increase in total transgene expression shown in FIG. 1, Panels A–E, was dramatically greater than the increase in the percent of 3T3 cells expressing β-galactosidase transgene, after applying adenovirus alone for 20 minutes. With the Ad2/βGal-2 alone only 3.5% of the cells stained blue (n=607 cells) after staining for β-galactosidase, whereas with Ad2/βGal-2:CaPi coprecipitates 99% of cells stained blue (n=800 cells). Ad:CaPi coprecipitates also enhanced expression in other cells that are relatively resistant to adenovirus infection (9 L gliosarcoma cells, a 130-fold increase compared to adenovirus alone, and primary cultures of human umbilical vein endothelial cells, a 150-fold increase). Likewise in cells that are easily infected Ad:CaPi coprecipitates provided a significant advantage over adenovirus alone (HeLa cells, a 9-fold increase, and COS cells, a 12-fold increase).

EXAMPLE 3

The effects of serum on the co-precipitates of the present invention were ascertained. In all experiments NIH 3T3 cells were treated with 40 MOI adenovirus for 20 minutes with the following variations: A) Ad:CaPi co-precipitates were formed in the absence of serum and then added to cells in the presence (+) or absence (−) of 10% FCS; B) Ad:CaPi co-precipitates were formed in the presence (+) of 10% FCS, or 10% FCS was added after formation of the precipitate (−); and C) Ad:CaPi co-precipitates or adenovirus and CaPi precipitates were added separately to cells in presence of 10% FCS. For A, B, and C, the $Ca^{2+}$ concentration was 5.8 mM, Pi concentration was 0.86 mM, and the precipitates were formed for 15–30 minutes.

Figure 2A:
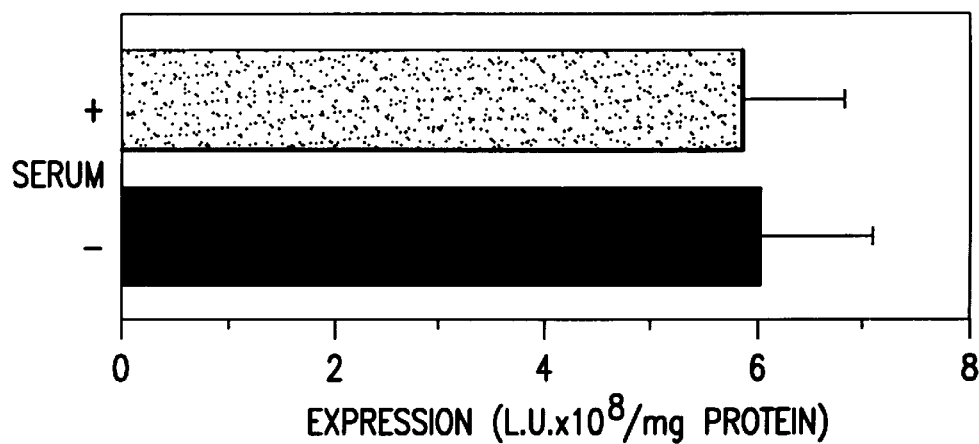
FIG. 2, Panels A–C, are bar graphs showing the effects of serum and Ad:CaPi co-precipitation on transgene expression in NIH 3T3 cells treated with 40 MOI adenovirus for 20 min.
Figure 2B:
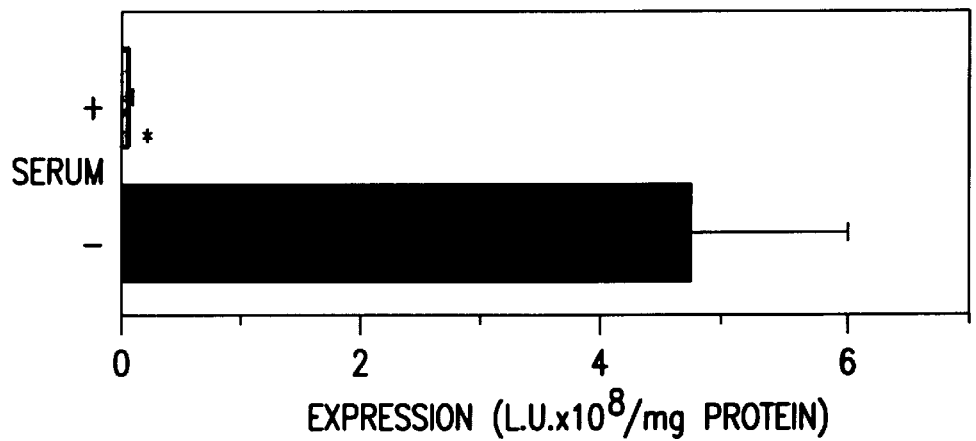
Figure 2C:
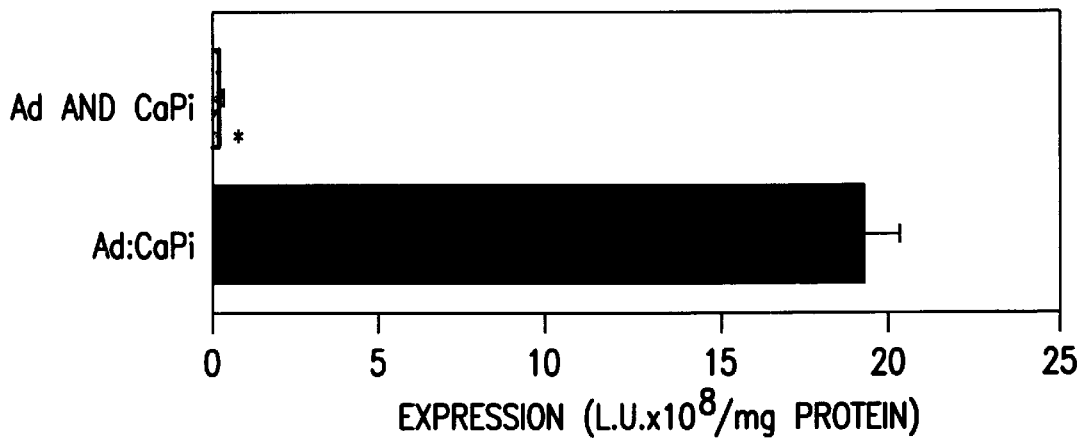

Data for these experiments are shown in FIG. 2, Panels A–C (asterisk indicates p<0.05; data are from one experiment (n=3) and each experiment was repeated at least 3 times). Panel A shows that co-precipitates can be added to serum without loss of efficacy. This illustrates that once the precipitate is generated, it is relatively stable. Panel B shows that when serum is added to the precipitating solution prior to precipitate formation the enhancement in gene transfer was abolished. This result suggests that serum interferes with formation of the Ad:CaPi co-precipitate. Panel C shows that CaPi precipitate when separately applied to cells in combination with adenovirus provided little enhancement of expression. Thus, the above experiments indicate that enhanced infection efficiency requires that adenovirus be included in the metal salt precipitate.

EXAMPLE 4

To assess binding of the co-precipitated adenoviral vectors, NIH 3T3 cells were treated with $2\times10^9$ particles of Cy3-labeled Ad2/βGal-2 for 60 minutes, rinsed with 3T3 media to remove unbound virus, and fixed with 4% paraformaldehyde. Cy3-labeled Ad2/βGal-2:CaPi coprecipitates were formed with 5.8 mM $Ca^{2+}$ and 0.86 mM Pi and applied to cells at 37° C. To ascertain the effects of temperature, binding studies of the adenovirus alone and as an Ad:CaPi co-precipitate were conducted at 4° C. and 37° C. Incubation at 4° C. was chosen since endocytosis is blocked at this temperature. In both experiments virus was placed on cells for 60 minutes and then removed by washing.

Figure 3A:
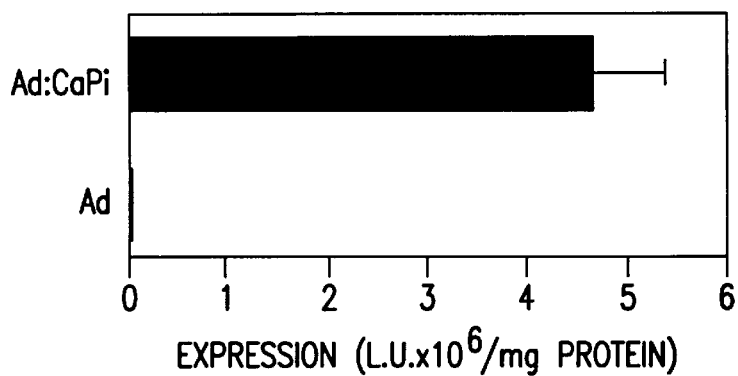
FIG. 3, Panels A and B, are bar graphs showing the effect of Cy3-labeled-Ad:CaPi co-precipitates on adenovirus association with NIH 3T3 cells: Panel A shows expression (top, n=3) and binding (bottom, n=5); and Panel B shows binding at 4° C. and 37° C. (n=5).
Figure 3B:
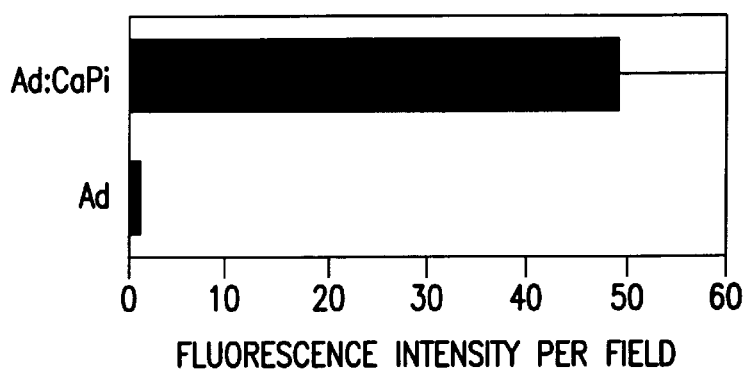
Figure 3C:
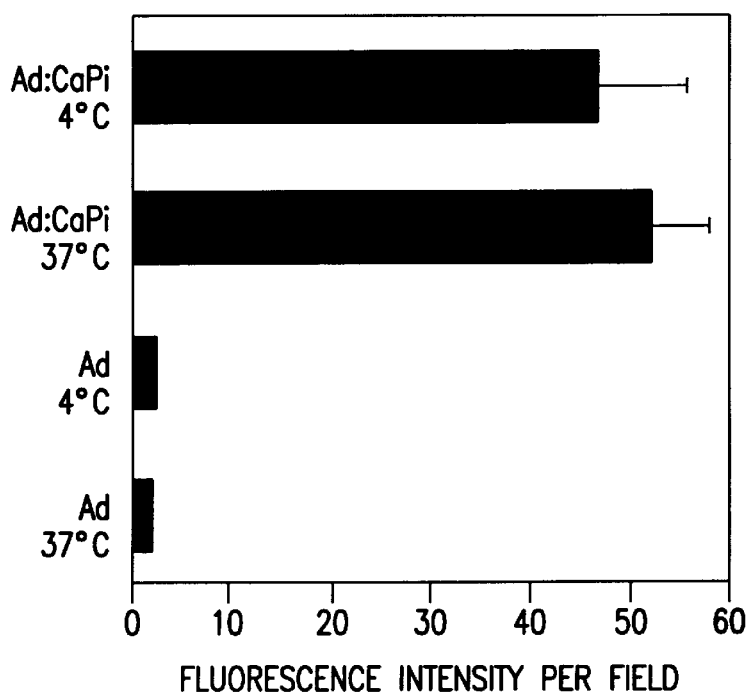

The results are shown in FIG. 3, Panels A and B. Panel A shows that an increase in transgene expression (top)(n=3) was parallel to an increase in viral binding (bottom)(n=5) for the Ad:CaPi co-precipitate, which were both dramatically improved over adenovirus alone. Panel B shows that incubation temperature has little effect on adenovirus binding, illustrating that adenoviral association is dependent on cellular mechanisms other than conventional endocytosis as with DNA:CaPi co-precipitates.

EXAMPLE 5

Figure 4A:
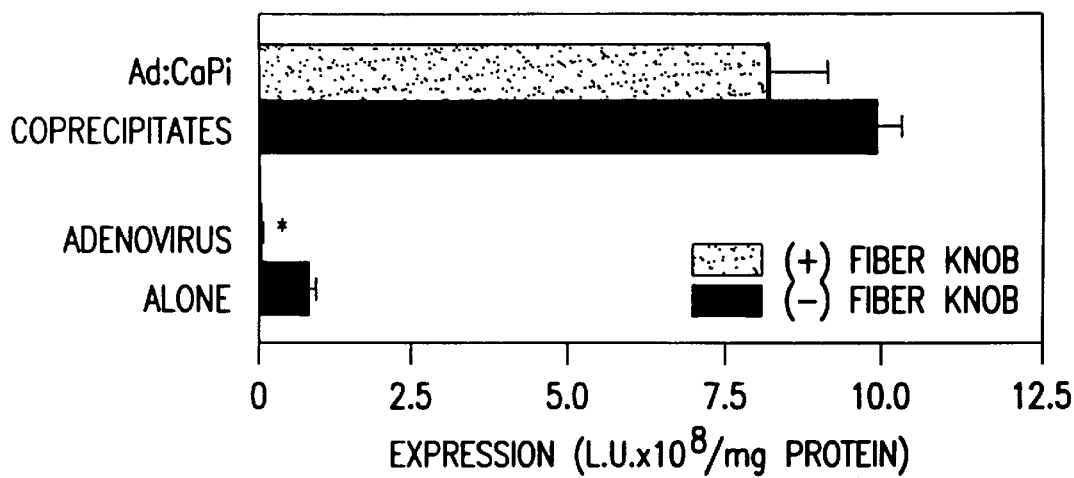
FIG. 4, Panels A and B, are bar graphs showing the following: Panel A the effect of fiber knob protein on transgene expression; Panel B the effects of heat inactivation, antibody inactivation, and substitution of plasmid DNA for adenovirus on transgene expression.
Figure 4B:
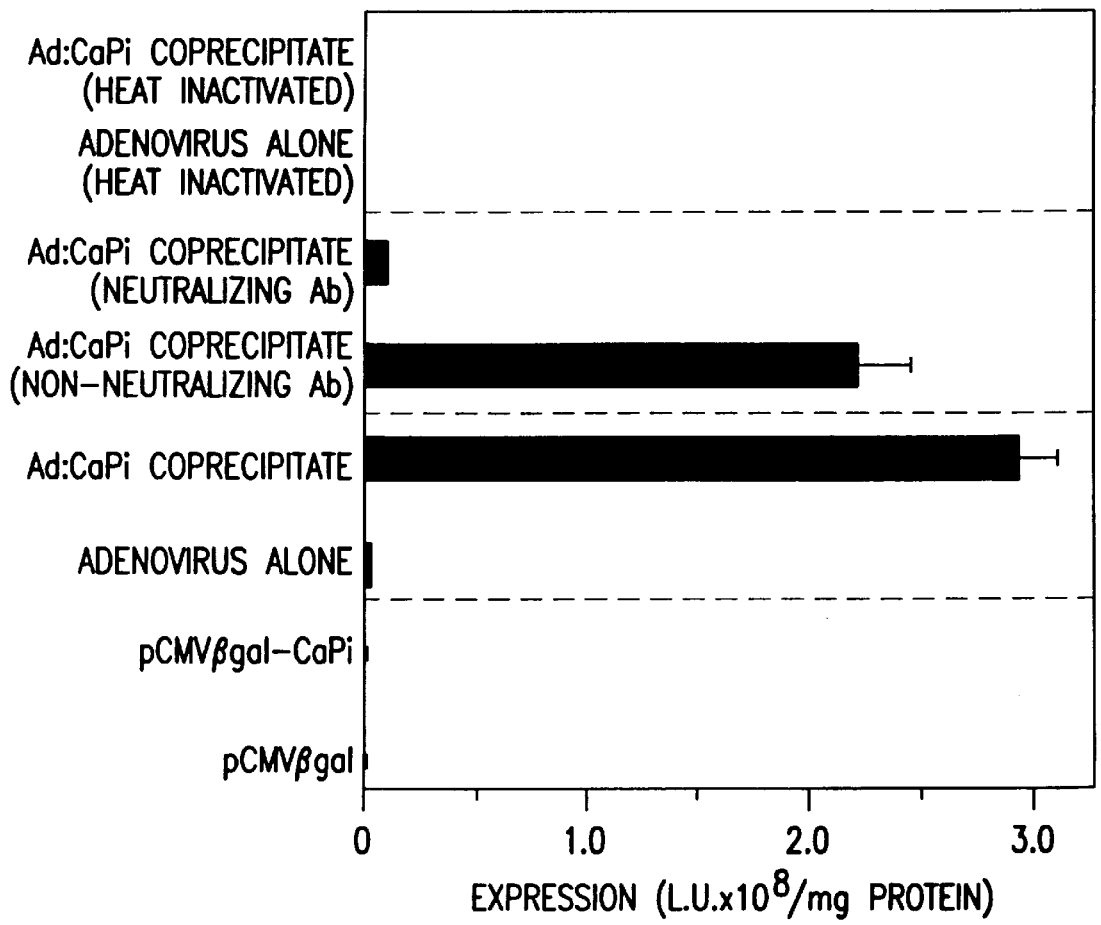

The ability of Ad:CaPi co-precipitates to enhance gene transfer to NIH 3T3 cells, which express little fiber receptor, suggested that binding of adenovirus fiber to its cell surface receptor was not required. To test this hypothesis directly, COS cells which are readily infected by adenovirus were studied. Fiber knob (0.7 μpg/ml) was added to cells for 10 minutes and then Ad:CaPi co-precipitates were applied in the continued presence of fiber knob. Cells treated with adenovirus received 40 MOI ($2 \times 10^9$ particles) and Ad-CaPi co-precipitates were prepared with 5.8 mM $Ca^{2+}$ and 0.86 mM Pi incubated for 15–30 minutes. The results are shown in FIG. 4, Panel A, with cells having fiber knob present depicted by shaded bars and cells absent fiber knob depicted by black bars (asterisk indicates $p<0.05$). Panel A shows that fiber knob protein inhibited transgene expression by adenovirus alone by 94%, as expected by conventional wisdom. However, no appreciable effect on transgene expression by Ad:CaPi co-precipitates was detected. These results show that adenovirus fiber is not required for the enhanced efficiency of infection utilizing the metal salt precipitates of the invention.

NIH 3T3 cells were treated with the following for 20 minutes to ascertain the effects: (1) adenovirus to be used alone or as a co-precipitate was heat inactivated at 60° C. for 30 minutes where indicated; (2) antibodies (neutralizing and non-neutralizing) were incubated with adenovirus for 30 minutes before co-precipitation; (3) Plasmid DNA (pCMV-βGal, 16.6 ng) was utilized alone or co-precipitated with CaPi under the same conditions used for adenovirus. The amount of plasmid DNA equaled approximately $2 \times 10^9$ plasmids. Cells treated with adenovirus received 40 MOI ($2 \times 10^9$ particles) and Ad-CaPi coprecipitates were prepared with 5.8 mM $Ca^{2+}$ and 0.86 mM Pi incubated for 15–30 minutes. Following intervention by one of the above described treatments, the vectors were removed and β-galactosidase activity was measured 24 hours later. Data are from one experiment (n=3) and each experiment was repeated 3 times.

The results are shown in Panel B. As is readily apparent from Panel B, heat inactivation, which disrupts viral proteins, inhibited transgene expression for adenovirus alone or as a CaPi co-precipitate. Similar results were obtained when adenovirus, before co-precipitate formation, was treated with a neutralizing anti-hexon antibody that presumably inhibits infection by interfering with steps subsequent to binding such as endosomal escape and traffic of viral DNA to the nucleus. Moreover, cells transfected with CaPi coprecipitates containing $2 \times 10^9$ plasmids encoding β-galactosidase exhibited little expression in comparison to precipitates formed with $2 \times 10^9$ particles of Ad2/βGal-2. These data demonstrate that although fiber is not necessary for infection with Ad:CaPi co-precipitates, other adenoviral proteins are required to facilitate gene transfer and expression. These results also explain why CaPi precipitates that contain adenovirus produce much more transgene expression than those containing DNA alone.

EXAMPLE 6

Figure 5A:
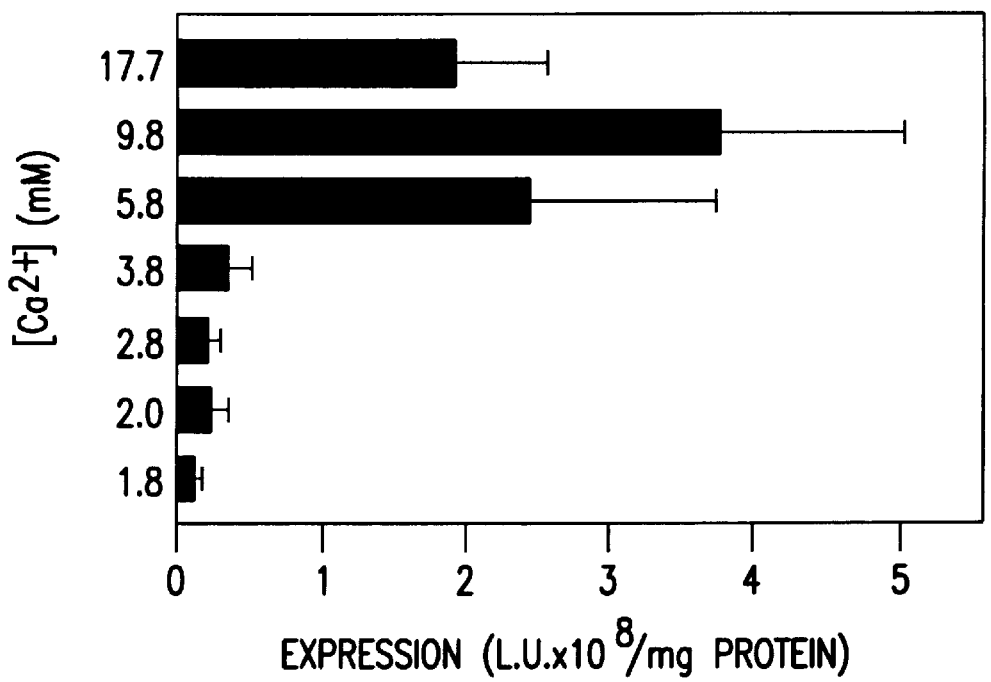
FIG. 5, Panels A and B, are bar graphs showing expression of β-galactosidase in normal airway epithelia in vitro and CFTR Cl⁻ current in CF airway epithelia in vitro: Panel A shows expression versus total $Ca^{2+}$ concentration; and Panel B shows CFTR Cl⁻ current of cells transfected with either Ad2/CFTR-16:CaPi at a 5.8mM $Ca^{2+}$ concentration or Ad2/CFTR-16 alone.
Figure 5B:
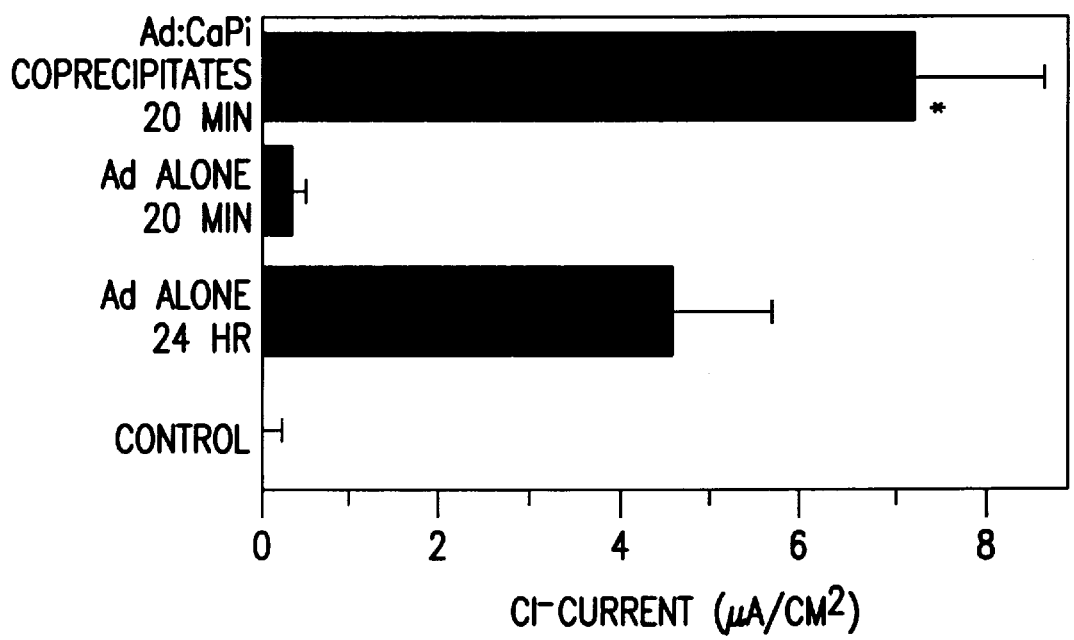

To evaluate gene transfer to airway epithelia, we studied primary cultures of human airway epithelia grown at the air-liquid interface were studied. Under these conditions, the epithelia differentiate and form a ciliated epithelium that is resistant to gene transfer by adenovirus and cationic lipid vectors (Zabner et al.(1996) *J. Virol.* 70:6994–7003; Fasbender, et al. (1997) *Gene Ther.* 4:1173–1180). Primary cultures of normal airway epithelia grown at the air-liquid interface were studied 14–20 days after seeding. Ad2/βGal-2 (at an MOI of 50) was applied to the apical surface of the epithelia for 20 minutes and then removed by washing. Three or 4 days later, β-galactosidase activity was measured as described in Example 1. The $Ca^{2+}$ concentration was varied between 1.8 to 17.7 mM with Pi concentration was 0.86 mM (n=9). The results of transgenic expression versus $Ca^{2+}$ concentration are shown FIG. 5, Panel A. FIG. 5, Panel A shows that when vector was applied to the apical surface for a short exposure time (20 minutes), Ad:CaPi co-precipitates enhanced transgene expression.

The ability of Ad:CaPi co-precipitates to transfer CFTR cDNA to CF airway epithelia grown at the air-liquid interface was tested by applying Ad2/CFTR-16 (at an MOI of 50) for 20 minutes. The $Ca^{2+}$ concentration was 5.8 mM with a Pi concentration of 0.86 mM. CFTR $Cl^-$ current was measured as described in Example 1. Briefly, the current was measured by inhibiting Na+ current with amiloride ($10^{-5}$ M), applying cAMP agonists, and then measuring the current inhibited by bumetanide (100 μM) applied to the basolateral surface. The results are shown in FIG. 1, Panel B (n=6, asterisk indicates $p<0.05$ compared to adenovirus alone for 20 minutes). Untreated CF epithelia which was used as a negative exhibited no $Cl^-$ current. As a positive control, Ad2/CFTR-16 was allowed to remain on the mucosal surface for 24 hours; this long incubation period allowed significant transgene expression and transepithelial $Cl^-$ transport increases into the normal range (Zabner et al.(1996) *J. Virol.* 70:6994–7003). As a comparative standard, adenovirus alone was applied to the mucosal surface for only 20 minutes, in which little $Cl^-$ current was exhibited, as previously reported (Zabner, et al. (1997) *J. Clin. Invest.* 100:1144–1149, Zabner et al.(1996) *J. Virol.* 70:6994–7003). However, the application of Ad:CaPi co-precipitates for 20 minutes resulted in $Cl^-$ current that was at least as large as that obtained following a 24 hours incubation with adenovirus alone. These data demonstrate that Ad:CaPi co-precipitates are much more efficient than adenovirus alone for the transfer of CFTR cDNA to differentiated airway epithelia and the generation of CFTR $Cl^-$ current indicating that a functioning chloride ion channel was present.

EXAMPLE 7

Figure 6A:
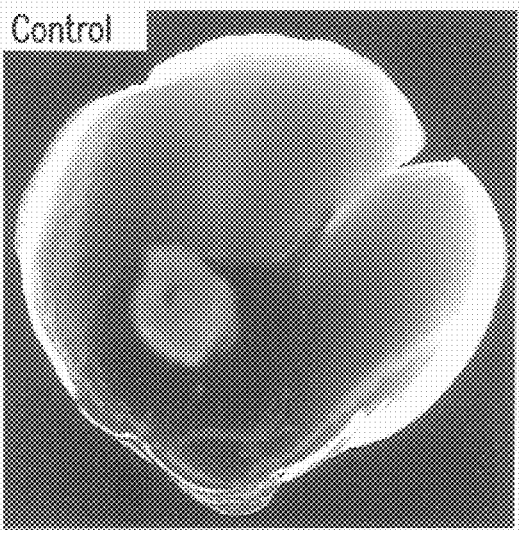
FIG. 6, Panels A–C, are photomicrographs of whole mouse lung stained with X-gal reagent: Panel A shows mouse lung treated with vehicle control; Panel B shows mouse lung treated Ad2/βpGal-2 (2×10$^8$ IU) alone; and Panel C shows mouse lung treated with Ad2/βGal-2 (2×10$^8$ IU) as a Ad: CaPi co-precipitate.
Figure 6B:
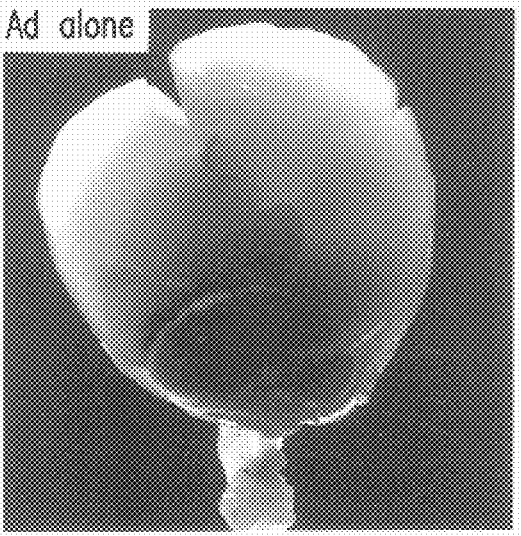
Figure 6C:
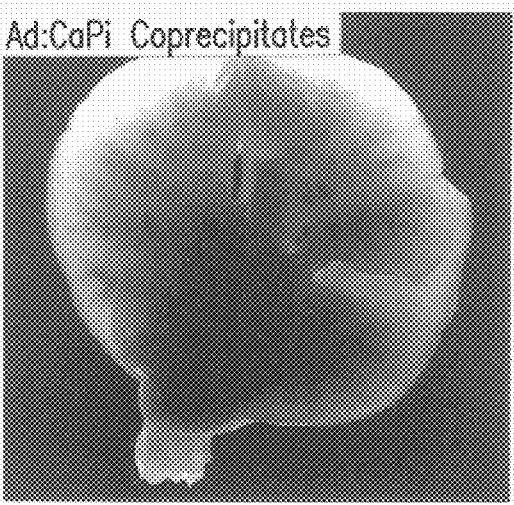

To investigate Ad:CaPi co-precipitates in vivo, Ad2/βGal-2 ($2 \times 10^8$ IU) was administered as virus alone or as Ad:CaPi co-precipitates to mouse lungs. The co-precipitates had $Ca^{2+}$ concentrations that ranged from 5.8, 12, 18, and 36 mM with a Pi concentration of 0.86 mM. In both experiments Ad2/βGal-2 ($2 \times 10^8$ I.U.) delivered by intranasal administration. This dose is lower than usually applied to obtain significant pulmonary gene transfer in order to ascertain whether delivery as a co-precipitate would enhance gene transfer. Three days following intranasal administration whole lungs were stained with X-gal reagent following the procedure set forth in Example 1. The results of X-gal staining is shown in FIG. 6, Panels A–C. Panel A shows that upon gross examination there was little evidence of staining. Panel B shows lung that received Ad2/βGal-2 alone appeared similar to lungs not treated with virus. In contrast, Panel C shows lungs treated with the same dose of virus delivered as Ad:CaPi coprecipitates (12 mM $Ca^{2+}$ and 0.86 mM Pi concentrations) exhibited significant X-Gal staining as readily apparent from the photomicrograph. Particularly striking was the pattern of X-Gal staining which traced the airways, rather than the parenchyma. Out of the co-precipitates with varying $Ca^{2+}$ concentrations (5.8, 12, 18, and 36 mM) tested, the co-precipitate that contained 12 mM $Ca^{2+}$ and 0.86 mM Pi was the most effective. Similar results were obtained with 6 animals in each group.

Figure 7A:
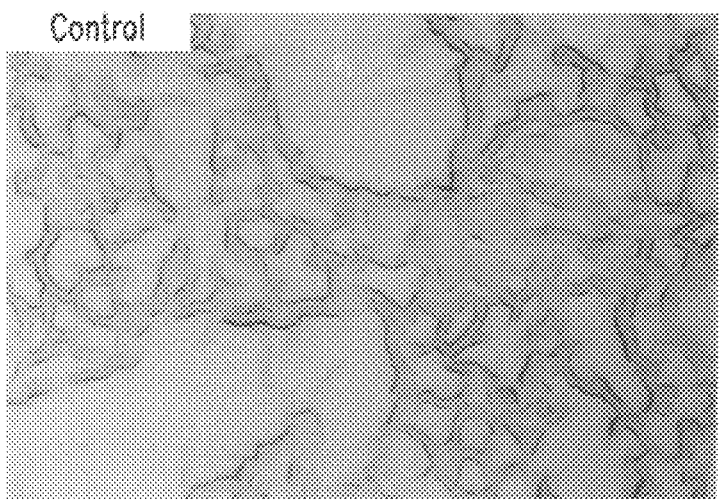
FIG. 7, Panels A–C, are photomicrographs of sections of the blue stained mouse lungs shown in FIG. 6: Panel A shows mouse lung treated with the vehicle control; Panel B shows mouse lung treated Ad2/βGal-2 (2×10$^8$ IU) alone; and Panel C shows mouse lung treated with Ad2/βGal-2 (2×10$^8$ IU) as a Ad:CaPi co-precipitate.
Figure 7B:
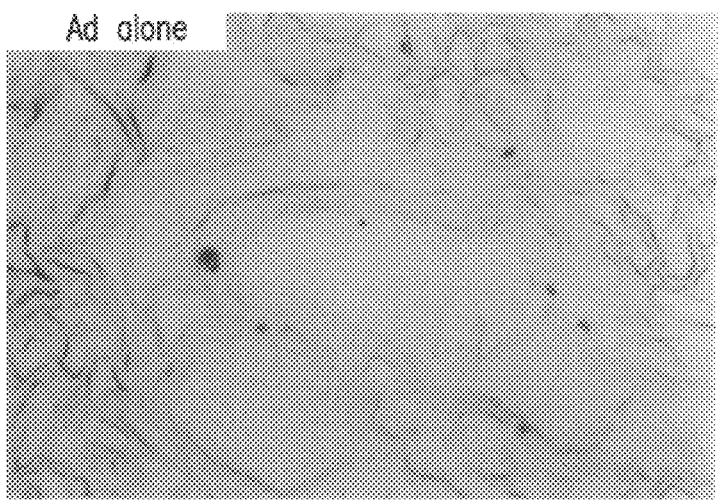
Figure 7C:
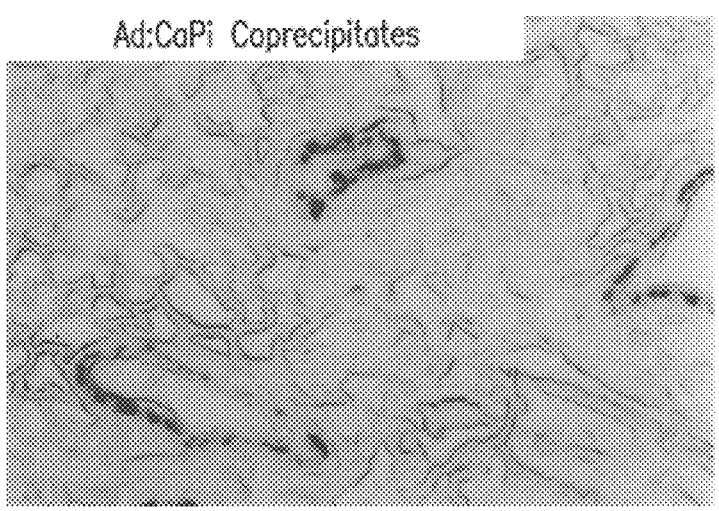

Sections of the X-gal stained lungs described above were taken. Representative photomicrographs from lungs treated with vehicle, adenovirus alone or Ad:CaPi coprecipitates are shown in FIG. 7, Panels A–C. Panel B shows that in sections from lungs treated with adenovirus alone, there were a few blue-stained cells in airways and in the parenchyma. In contrast, Panel C shows a field from a lung treated with Ad:CaPi co-precipitate of the present invention in which most small and medium-sized airways showed positively-stained cells. Staining was predominantly in the airways with only rare positive cells in the parenchyma.

Figure 8:
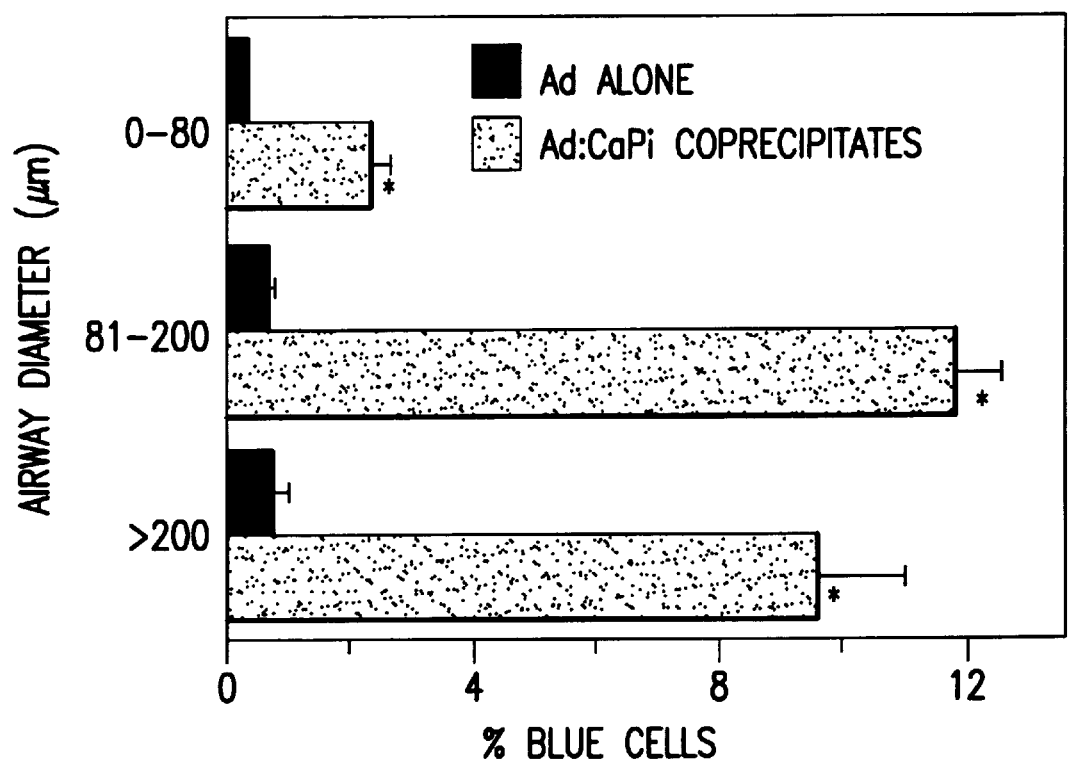
FIG. 8 is a bar graph showing the percentage of mouse airway epithelium cells in vivo stained with X-gal reagent according to airway diameter and treatment with Ad2/βGal-2 alone or Ad2/βGal-2:CaPi co-precipitate.

Blue-stained cells were counted in sections of lungs following the procedure set forth in Example 1. Percentage blue cells was determined for airways of airway diameters of 0–80 μm, 80–200 μm and over 200 μm. Data was compiled from 50–200 airways. The quantitative assessment of expression is shown in FIG. 8 (asterisk indicates p<0.05). Readily apparent from FIG. 8 is that in each airway region more cells expressed the transgene after administration of Ad:CaPi coprecipitates than adenovirus alone. Thus, FIG. 8 conclusively shows that the adenoviral vector/metal salt co-precipitates of the present invention enhance transgene expression in vivo.

We claim:

1. A co-precipitate for facilitating infection by adenovirus vectors comprising a co-precipitate of a metal salt and adenoviral vectors wherein said adenovirus vectors comprise a transgene and wherein said co-precipitate is free of non-adenoviral proteins and peptides.

2. The co-precipitate of claim 1 wherein the cation of said metal salt is a divalent cation.

3. The co-precipitate of claim 2 wherein said divalent cation is an alkaline earth metal.

4. The co-precipitate of claim 2 wherein said divalent cation is a transition-state metal.

5. The co-precipitate of claim 1 wherein the anion of said metal salt is a phosphate, a carbonate, a sulfide or a mixture thereof.

6. The co-precipitate of claim 1 wherein said metal salt is calcium phosphate.

7. The co-precipitate of claim 1 wherein said transgene encodes a cystic fibrosis transmembrane conductance regulator protein.

8. A composition comprising the co-precipitate of claim 1 and a carrier.

9. A method of making a co-precipitate for facilitating infection by adenovirus vectors, which comprises precipitating in serum-free media a metal salt in the presence of adenovirus vectors comprising a transgene to form said co-precipitate having said adenovirus vectors dispersed therein.

10. The method of claim 9 wherein said co-precipitate is dispersed in a carrier.

11. The method of claim 9 wherein the cation of said metal salt is a divalent cation.

12. The method of claim 9 wherein said divalent cation is an alkaline earth metal.

13. The method of claim 9 wherein said divalent cation is a transition-state metal.

14. The method of claim 9 wherein the anion of said metal salt is a phosphate, a carbonate, a sulfide or a mixture thereof.

15. The method of claim 9 wherein said metal salt is calcium phosphate.

16. The method of claim 9 wherein said transgene encodes a cystic fibrosis transmembrane conductance regulator protein.

17. A method for delivering a transgene to a target cell, which comprises precipitating in a serum-free media a metal salt in the presence of adenovirus vectors comprising said transgene to form a co-precipitate having said adenovirus vectors dispersed therein, and administering said co-precipitate to a target cell thereby facilitating infection of the target cell.

18. The method of claim 17 wherein the cation of said metal salt is a divalent cation.

19. The method of claim 18 wherein said divalent cation is an alkaline metal.

20. The method of claim 18 wherein said divalent cation is a transition-state metal.

21. The method of claim 17 wherein the anion of said metal salt is a phosphate, a carbonate, a sulfide or a mixture thereof.

22. The method of claim 17 wherein said metal salt is calcium phosphate.

23. The method of claim 17 wherein said transgene encodes cystic fibrosis transmembrane conductance regulator.

24. The method of claim 17 wherein said target cell is an airway epithelial cell.

25. A method of providing cystic fibrosis transmembrane conductance regulator to airway epithelial cells of an individual with cystic fibrosis which comprises precipitating in a serum-free media a metal salt in the presence of adenovirus vectors containing a transgene encoding cystic fibrosis transmembrane conductance regulator to form a co-precipitate, and administering said co-precipitate to the airway epithelial cells of said individual with cystic fibrosis, under conditions whereby said transgene is expressed and a functional chloride ion channel is produced in the airway epithelial cells of said individual.

26. The method of claim 25 wherein said co-precipitate is delivered to said airway epithelial cells by inhalation.

27. A co-precipitate for facilitating infection by adenovirus vectors, said precipitate being prepared by the step of precipitating in a serum-free media a metal salt in the presence of adenovirus vectors comprising transgenes to form said co-precipitate having said adenovirus vectors dispersed therein.

\* \* \* \* \*

UNITED STATES PATENT AND TRADEMARK OFFICE
CERTIFICATE OF CORRECTION

PATENT NO.   : 6,086,870  
DATED        : July 11, 2000  
INVENTOR(S)  : Welsh et al.

Page 1 of 1

It is certified that error appears in the above-identified patent and that said Letters Patent is hereby corrected as shown below:

Column 1,  
Line 52, "Therapv" should read -- Therapy --

Column 2,  
Line 22, "omithine" should read -- ornithine --  
Line 39, "dysfumctional" should read -- dysfunctional --

Column 5,  
Line 2, "treated" should read -- treated with --  
Line 8, "treated" should read -- treated with --

Column 6,  
Line 27, "serumfree" should read -- serum-free --  
Line 60, "partifacilitatefacilitates" should read -- particle size facilitates --

Column 7,  
Line 12, "e.," should read -- e.g., --

Column 20,  
Line 29, "cystic" should read -- a cystic --

Signed and Sealed this

Fourteenth Day of October, 2003

JAMES E. ROGAN  
*Director of the United States Patent and Trademark Office*